United States Patent
Àwengen et al.

(10) Patent No.: US 7,871,439 B2
(45) Date of Patent: Jan. 18, 2011

(54) AUDITORY OSSICLE PROSTHESIS WITH TUNING OPTION

(75) Inventors: Daniel Felix Àwengen, Binningen (CH);
Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 509 days.

(21) Appl. No.: 10/586,718

(22) PCT Filed: Jan. 20, 2005

(86) PCT No.: PCT/EP2005/000528

§ 371 (c)(1),
(2), (4) Date: Apr. 28, 2008

(87) PCT Pub. No.: WO2005/070237

PCT Pub. Date: Aug. 4, 2005

(65) Prior Publication Data

US 2008/0208337 A1    Aug. 28, 2008

(30) Foreign Application Priority Data

Jan. 23, 2004   (DE) .................. 20 2004 001 008 U (51) Int. Cl.
*A61F 2/18*        (2006.01)
(52) U.S. Cl. ........................................... 623/10
(58) Field of Classification Search .................. 623/10; 600/25
See application file for complete search history.

(56) References Cited

U.S. PATENT DOCUMENTS

| | | | |
|---|---|---|---|
| 3,710,399 A * | 1/1973 | Hurst ........................... | 623/10 |
| 4,655,776 A | 4/1987 | Lesinski | |
| 5,554,188 A * | 9/1996 | Prescott ........................ | 623/10 |
| 6,387,128 B1 * | 5/2002 | Kurz et al. .................... | 623/10 |
| 7,553,328 B2 * | 6/2009 | Steinhardt et al. ............. | 623/10 |
| 2001/0037151 A1 * | 11/2001 | Knox et al. ................... | 623/10 |
| 2002/0045939 A1 * | 4/2002 | Kurz ............................ | 623/10 |
| 2005/0027357 A1 | 2/2005 | Steinhardt et al. | |

FOREIGN PATENT DOCUMENTS

| | | |
|---|---|---|
| DE | 203 10 609 | 10/2003 |
| EP | 1 181 907 | 2/2002 |
| WO | 90/07915 | 7/1990 |
| WO | 90/11737 | 10/1990 |
| WO | 95/01710 | 1/1995 |
| WO | 99/15111 | 4/1999 |

* cited by examiner

*Primary Examiner*—Suzette J Gherbi
(74) *Attorney, Agent, or Firm*—Michael J. Striker (57) ABSTRACT

An auditory ossicle prosthesis (40) which replaces or bridges at least one element in the human auditory ossicle chain, whereby the auditory ossicle prosthesis (40) is made of an elastic material or a material having at least one articulated connection, is characterised in that means for frequency adjustment (=tuning) are arranged for sound transmission in the middle ear, in particular to change the lever conditions in the auditory ossicle chain. In this way sound transmission between the middle ear area and the inner ear of the human auditory canal is considerably improved, whereby, in particular, optimum adaptation to the individually differing conditions and a tailor-made solution to the problems and deficiencies in the patient in question are made possible.

18 Claims, 8 Drawing Sheets

AUDITORY OSSICLE PROSTHESIS WITH TUNING OPTION

CROSS-REFERENCE TO A RELATED APPLICATION

The invention described and claimed hereinbelow is also described in German Patent Application DE 20 2004 001 008.9 filed on Jan. 23, 2004. This German Patent Application, whose subject matter is incorporated here by reference, provides the basis for a claim of priority of invention under 35 U.S.C. 119(a)-(d).

The invention relates to an auditory ossicle prosthesis which replaces or bridges at least one section of the human auditory ossicle chain, whereby the auditory ossicle prosthesis (10) is made of an elastic material or a material having at least one articulated joint.

An auditory ossicle prosthesis of this type is known, for example, from EP 1 181 907 B2.

Auditory ossicle prostheses are used in the case of an entirely or partially missing or damaged auditory ossicle in the human middle ear to transmit sound from the ear drum to the inner ear. The auditory ossicle prosthesis has two ends, whereby, depending on the specific circumstances one end of the auditory ossicle prosthesis is, for example, attached to the anvil projection of the human auditory ossicle chain and the other end of the auditory ossicle prosthesis is, for example attached to the stapes bone of the human auditory ossicle chain or is directly immersed in the inner ear.

As the anatomical circumstances of the ear, such as the position, shape and size of the stapes bone, the anvil, the hammer and the ear drum vary, it is advantageous if auditory ossicle prostheses are not made rigid, but exhibit a certain flexibility or variability. In order to achieve this flexibility/variability various fastening and connection devices for auditory ossicles which have elastic components and/or joints are known. In many cases with the known auditory ossicle prostheses only limited transmission of sound between the ear drum and the inner ear is possible as they can only replace the natural anatomical forms for the auditory ossicle chain to a very limited extent.

SUMMARY OF THE INVENTION

In view of this the aim of the invention is to modify an auditory ossicle prosthesis of the type described in the introduction in such a way that the transmission of sound between the middle ear area and the inner ear of the human auditory canal is considerably improved, whereby, in particular, optimum adaptation to the individually different circumstances and tailor-made solutions to the problems and deficiencies in the patient in the question are made possible.

In accordance with the invention this task is achieved in an elegant and effective manner in that means are provided for adjusting the frequency (=tuning) or sound conduction in the middle ear, in particulate to adjust the lever conditions in the auditory ossicle chain.

In contrast to known devices the auditory ossicle prosthesis in accordance with the invention has the essential advantage that frequency-dependent improvement in hearing can be specifically achieved. For example, hearing problems in the form of so-called holes in the audible frequency band which manifest themselves in a dramatic reduction in the hearing of patients in certain, often relatively narrow ranges of the individual hearing range depicted by means of an audiogram, can be specifically eliminated or at least considerable alleviated through appropriate tuning. The resulting achievable hearing result in the patient can be very considerably improved in this way. Also, the idea in accordance with the invention opens up a large number of different interventional and approach possibilities with regard to the individual treatment of hearing problems in the middle ear area which go far beyond the treatment possibilities using known auditory ossicle prostheses.

In a preferred class of forms of embodiment of the invention the transition from the anvil projection to the stapes bone is largely copied from the anatomical circumstances of the natural auditory ossicle chain. In particular these forms of embodiment are characterised in that the prosthesis is attached on the one hand to the anvil projection and on the other hand to the stapes bone or is directly inserted into the inner ear, starting from its coupling on the anvil projection follows the natural anvil projection to its end or beyond, and in the area of the natural end of the anvil projection runs at an angle to the other end point of the auditory ossicle prosthesis on the stapes bone or on/in the inner ear.

The prosthesis can be attached to the anvil projection approximately 1 mm behind the distal end of the projection and via the orientation of the prosthesis in the direction of the course of the natural projection, lever conditions can be achieved/simulated, which correspond to the natural conditions as far as possible. The prosthesis is angled in an articulated or elastic manner so that, as in the natural auditory ossicle chain, sound transmission can be adapted to the spatial conditions in the middle ear. The lever conditions are considerable improved vis-à-vis the prostheses known from the prior art so that with the new prosthesis much better hearing comfort is achieved.

The prosthesis in accordance with the invention can itself be made of tissue and bone-compatible synthetic material, composite fibre materials or metals, which support/guarantee the movability of the angled shape of the prosthesis in accordance with the invention.

In a preferred embodiment of the invention the prosthesis is attached by means of a first clip to the anvil projection on which a first rod is arranged with an end in the shape of a ball which is arranged in a U-shaped socket component which gradually becomes a second rod ending as a piston or in further clip.

With this embodiment of the auditory ossicle prosthesis in accordance with the invention a high degree of movability is achieved, which supports improved sound transmission in the middle ear. By way of the ball joint a very high degree of movability of the prosthesis in accordance with the invention is achieved and this in a course modelled from the human auditory ossicle chain.

If the prosthesis in accordance with the invention is attached to the stapes bone or anvil projection by way of clips or by way of a piston, or is directly inserted into the inner ear via a piston, the flexibility or movability of the prosthesis in accordance with the invention is not impaired.

A particularly preferred form of embodiment of a joint in the angled area of the prosthesis is achieved by way of a ball and U-shaped socket component, in which the ball is arranged in the sides wall of the socket component in openings in the socket component. With an embodiment designed in this way the ball in the U-shaped socket component can move without restriction in all directions and guarantee sound transmission solutions in the best possible way in a relatively confined middle ear space.

In further form of embodiment of the invention the first and/or further clip are formed of two V- or U-shaped flexible tongues. The hold of a clip is improved by such a design. If the contact points of the clips are roughened at the points where they are in contact with the anvil projection/on the stapes bone, secure, durable fastening of the auditory ossicle prosthesis in accordance with the invention is guaranteed through increased friction and the resulting close connection.

To facilitate positioning of the auditory ossicle prosthesis in accordance with the invention a holding grip is arranged on the first and/or further clip. This embodiment facilitates the application of the prosthesis in accordance with the invention in the middle ear and reduces the risk of damaging the prosthesis during surgical implantation.

The auditory ossicle prosthesis in accordance with the invention can be designed as a piston at one end which is directly inserted into the inner ear. In this form of embodiment a further clip is unnecessary. More particularly, the prosthesis can by opening the human cochlea (=cochleotomy) be connected directly to the inner ear at one end. In this way a particularly long lever arm is achieved so that the intensification effect is optimal due to the lever path and the correspondingly large excursion.

In a further class of forms of embodiment of the invention the prosthesis can on the one hand be attached to the hammer (=malleus) and on the other to the anvil or stapes bone or, as described above, be inserted directly into the inner ear. In this way the treating doctor is provided with a great variability in the selection of treatment methods adapted to the individual case. In this way all possible defects and problems in the patient's middle ear area can be treated in a tailor-made manner.

The lever path and the thereby achieved excursion are greater the nearer to the end point (=umbo) of the hammer the prosthesis is arranged. Therefore further embodiments of the above forms of embodiment can be advantageous in which the prosthesis is arranged on or directly next to the umbo. This makes for a high amplification effect for the sound signal to be transmitted through the middle ear to the inner ear.

The auditory ossicle prosthesis in accordance with the invention is itself made of a biocompatible material/composite material, which rules out toxic reactions in the middle ear area and prevents irritation due to the implant material as far as possible.

In forms of embodiment of the invention, the prosthesis or parts thereof can be made of biocompatible synthetic materials or synthetic material components, in particular silicone, or composite fibre materials, which open up optimum treatment possibilities for the therapist.

In further forms of embodiment the prosthesis can also contain metal components of titanium and/or gold and/or tantalum and/or an alloy of these metals, whereby the ductility and good sterilisability of the materials can be exploited. When using metal components the prosthesis can be easily visualised in tomographic imaging using magnetic resonance.

It can also be of advantage to produce the prosthesis or parts thereof from a memory effect material, in particular nitinol. This allows, in particular, contact free coupling of the prosthesis when implanted in the target area of the middle ear.

The prosthesis itself can be made completely or only partially of one or more of the above metals.

In preferred forms of embodiment of the invention the tuning means can comprise a device for changing the articulation point of the prosthesis on the hammer and/or on the anvil projection and/or the stapes bone and/or on the inner ear depending on a predetermined frequency. In this way the therapist is provided with a high degree of variability in selecting the optimum prosthesis in dependence on the situation present in the middle ear of the patient.

In order to be able to individually adapt the auditory ossicle prosthesis in accordance with the invention particularly well individually to the complex and in each case differently shaped structures in the middle ear, for example to avoid impermissible mechanical contact with the numerous nerve paths located in the middle ear, it may be advantageous if in the form of embodiment in accordance with the invention the means for tuning comprise lever elements, the effect lengths/level conditions of which can be changed in dependence on a predetermined frequency response.

In advantageous further developments of these forms of embodiment, the lever elements comprise a lever section that prolongs the natural end of the anvil projection. In this way, for example, in the case of congenital or pathological shortening of the anvil projection a normal or the original structure and course of the auditory ossicle change can be produced/reconstructed.

A simple and in terms of effect (relatively) easily previously determinable mechanical influencing of the acoustic reaction of an auditory ossicle chain to be treated can be achieved in that the mass distribution of the individual parts of the prosthesis is calculated as a function of the required, predeterminable frequency response of the sound transmission in the middle ear.

It is particularly simple to produce a form of embodiment of the invention in which an at least one additional mass is attached to a part of the auditory ossicle chain in dependence on a required, predeterminable frequency response of the sound transmission. This can, if required, be combined with the above measure as fine tuning. This allows the impedance or the spectrum of the resonance frequencies of the chain to be individual moved in a required direction within precisely predeterminable boundaries without great cost.

In intra-operatively easy to use further embodiments of the above forms of invention the additional mass is attached to a part of the auditory ossicle chain by way of a clip.

Finally, forms of embodiment of the auditory ossicle prosthesis in accordance with the invention can also be combined with an active vibration section of an active implantable hearing aid in order to facilitate the care of patients with inner and outer ear impaired hearing.

Further features and advantages of the invention are set out in the following detailed description of examples of embodiment of the invention with the aid of the drawings, which show details essential to the invention, as well as in the claims. The individual features can be realised individually or combined in any combinations in variants of the invention.

In the schematic drawing examples of embodiment of the auditory ossicle prosthesis in accordance with invention are shown which will be described more detail in the following description. The forms of embodiment shown in the drawing are to be understood as examples and do not necessarily show the subject matter of the invention to scale.

DESCRIPTION OF THE PREFERRED EMBODIMENTS

Figure 1:
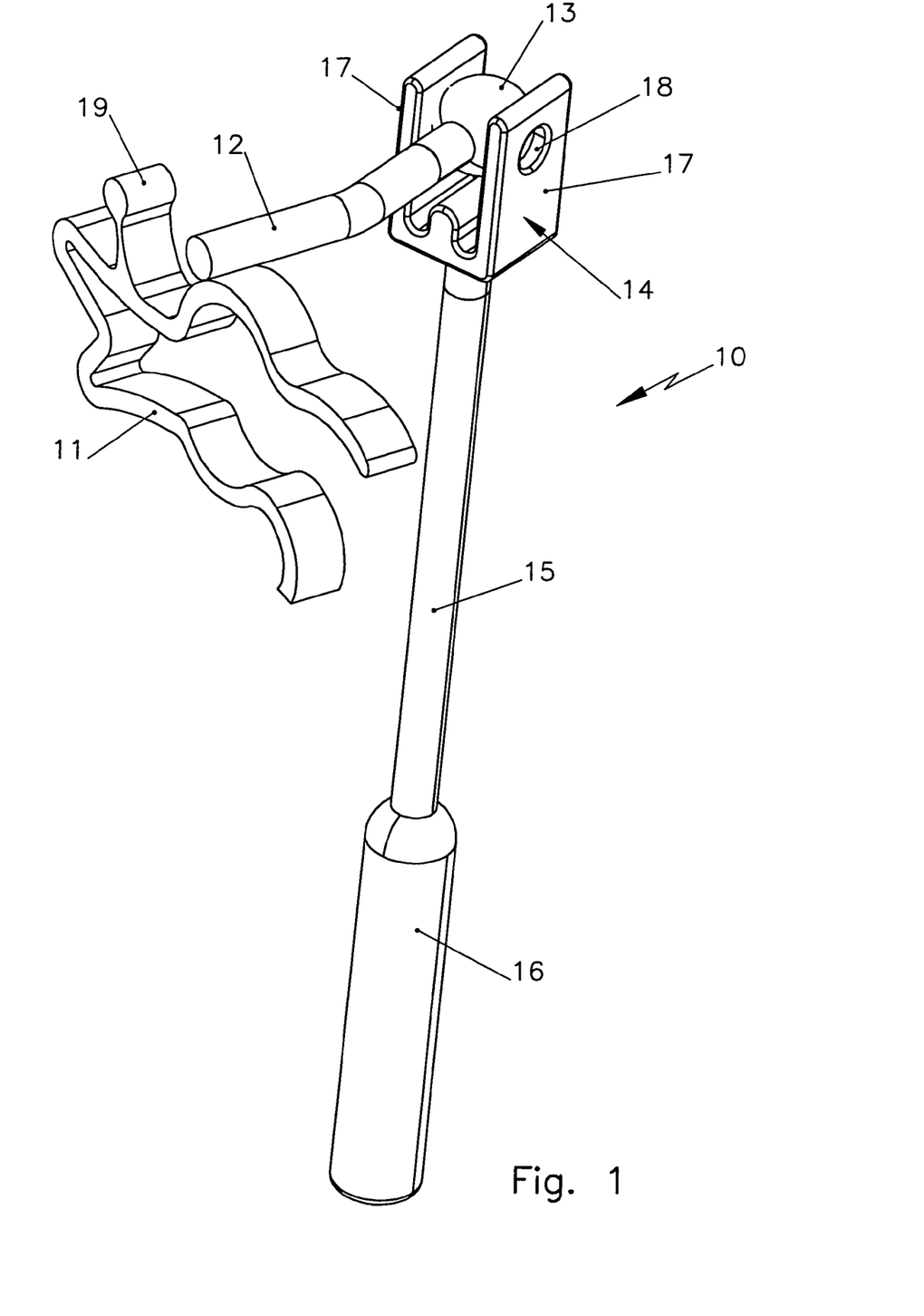
FIG. 1 shows an auditory ossicle prosthesis in accordance with the invention in a spatial view with a bend designed as a joint

FIG. 1 shows a perspective view of an auditory ossicle prosthesis 10 in accordance with the invention having a first clip 11, to which a first rod 12 is attached. The first rod 12 is slightly angled, it must not be straight. The rod 12 is materially fitted to the first clip 11 which is designed as a highly flexible V-shaped clip. The first clip 11 as well as the first rod 12 can be made of a titanium alloy.

The first rod 12 ends, opposite the first clip 11, in a ball 12, which is arranged in a U-shaped socket component 14. Connected to the U-shaped socket component 14 is a second rod 15, which becomes a piston 16. Instead of the piston 16, a further clip can be arranged on the second rod 15. Via the first clip 11 or the piston 16 or the further clip alternatively arranged on the end of the second rod 15 the auditory ossicle prosthesis 10 in accordance with the invention is held in the middle ear on the one hand on the anvil projection and on the other hand on the stapes and/or on/in the inner ear.

The U-shaped socket component 14 has side walls 17 in each of which there is an opening 18. The ball 13 is held in an articulated manner in these openings 18 so that a high degree of movability of the auditory ossicle prosthesis 10 is provided between the first clip 11 and the piston 16. A holding grip 19 is arranged on the first clip 11 by way of which the positioning of the first clip 11 on the anvil projection is facilitated.

Figure 2:
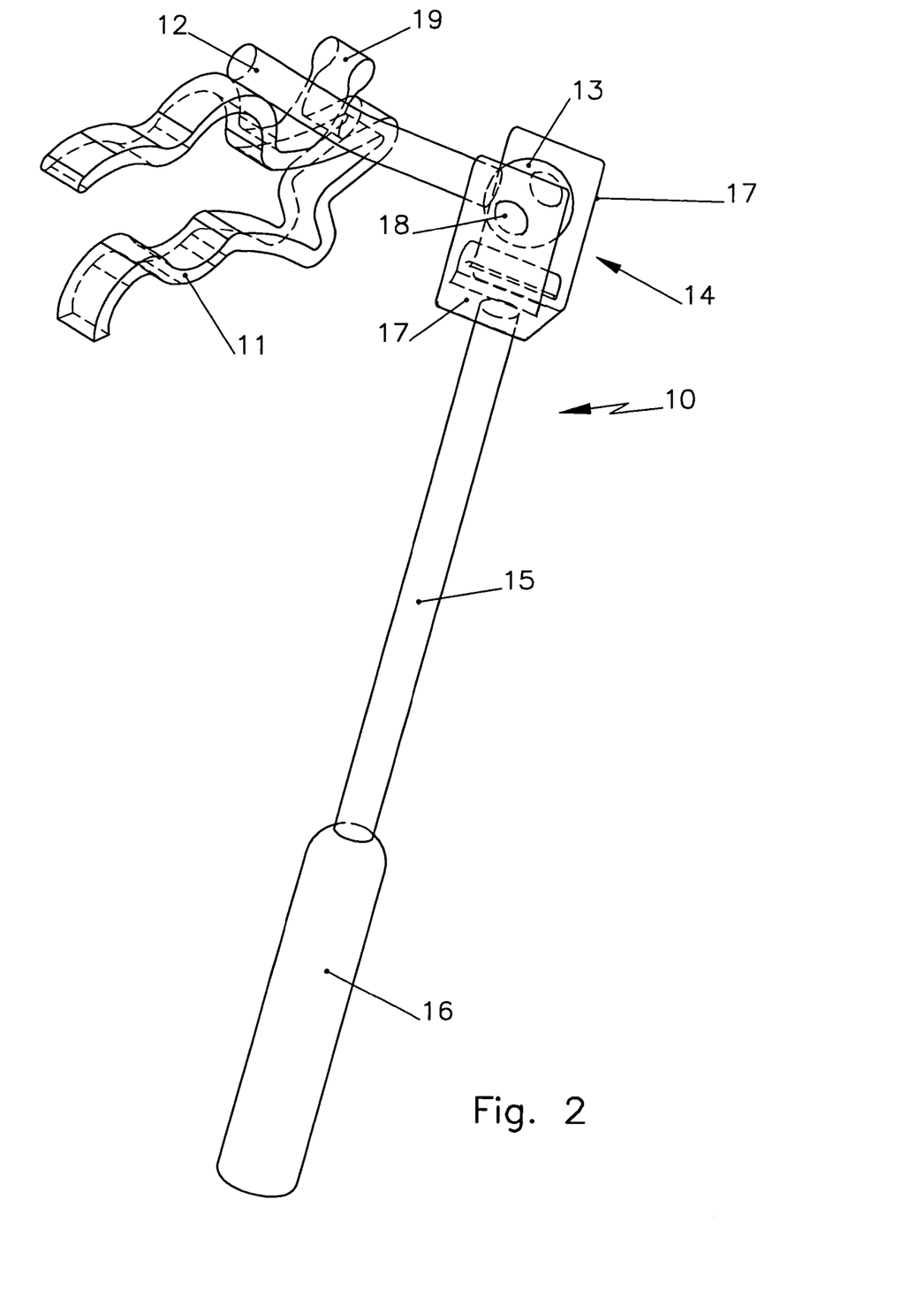
FIG. 2 shows an auditory ossicle prosthesis in accordance with FIG. 1 from another viewing angle.

FIG. 2 shows the auditory ossicle prosthesis 10 in accordance with the invention from FIG. 1 in a further perspective view from a different angle whereby the same features with the same reference numbers are provided. The attachment of the first rod 12 on the second rod 15 via the U-shaped socket component 14 can be clearly seen and the high degree of movability of the ball 13 in the openings 18 of the side walls 17 of the U-shaped socket component 14 is also clearly shown. If the auditory ossicle prosthesis 10 in accordance with the invention is placed in the middle ear, the ball joint has a high degree of movability between the first clip 11 and the piston 16.

Figure 3:
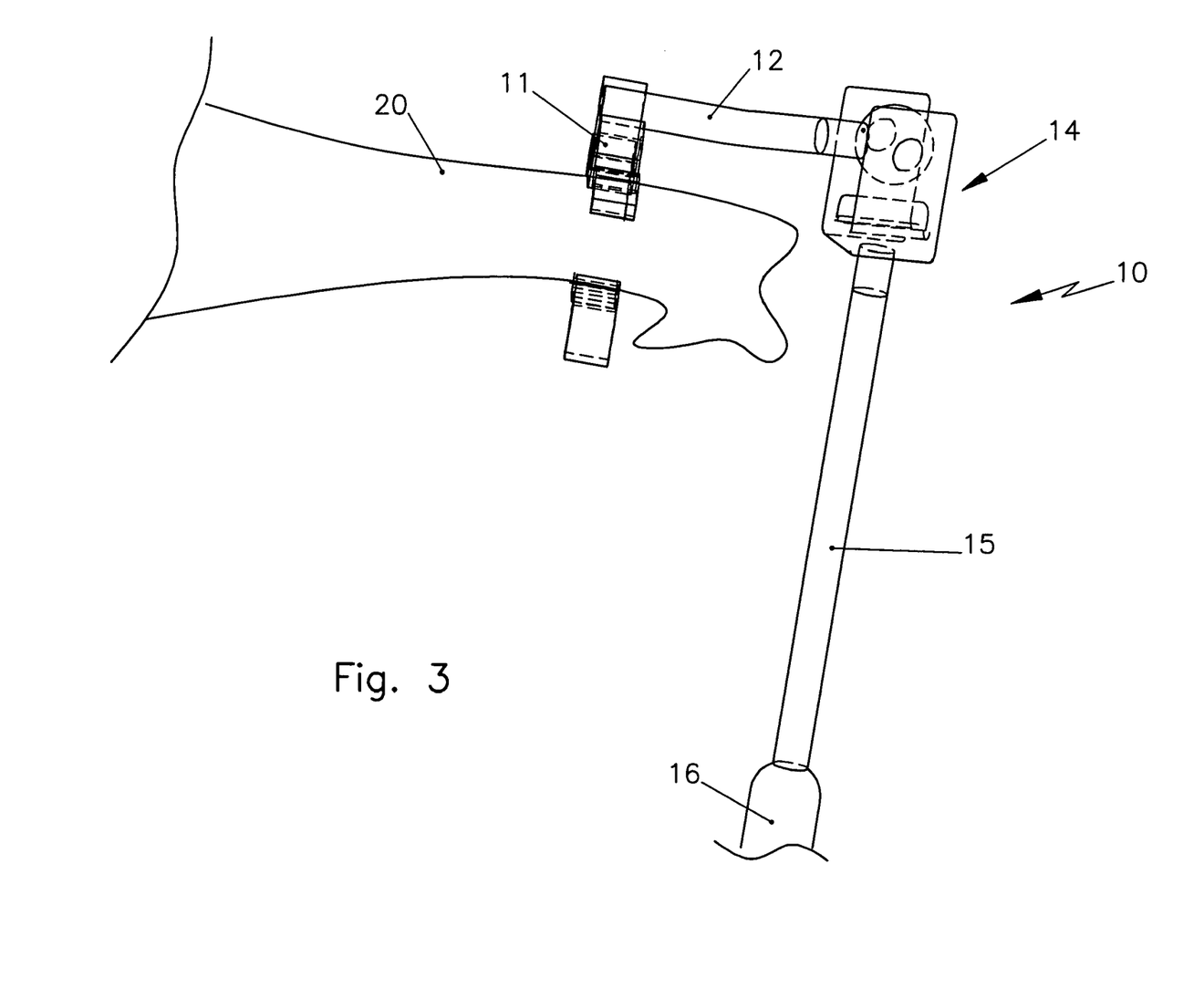
FIG. 3 shows a section of an auditory ossicle prosthesis in accordance with FIGS. 1 and 2, how it is jointed/attached to the anvil projection.

FIG. 3 shows a section of both an anvil projection 20 and the auditory ossicle prosthesis 10 shown in FIGS. 1 and 2 and how it is attached to the anvil projection 20 via the first clip 11. The auditory ossicle prosthesis 10 projects beyond the natural anvil projection 20 in that the first rod 12, connected in an articulated manner, becomes the second rod 15, which ends in the partially shown piston 16.

Figure 4A:
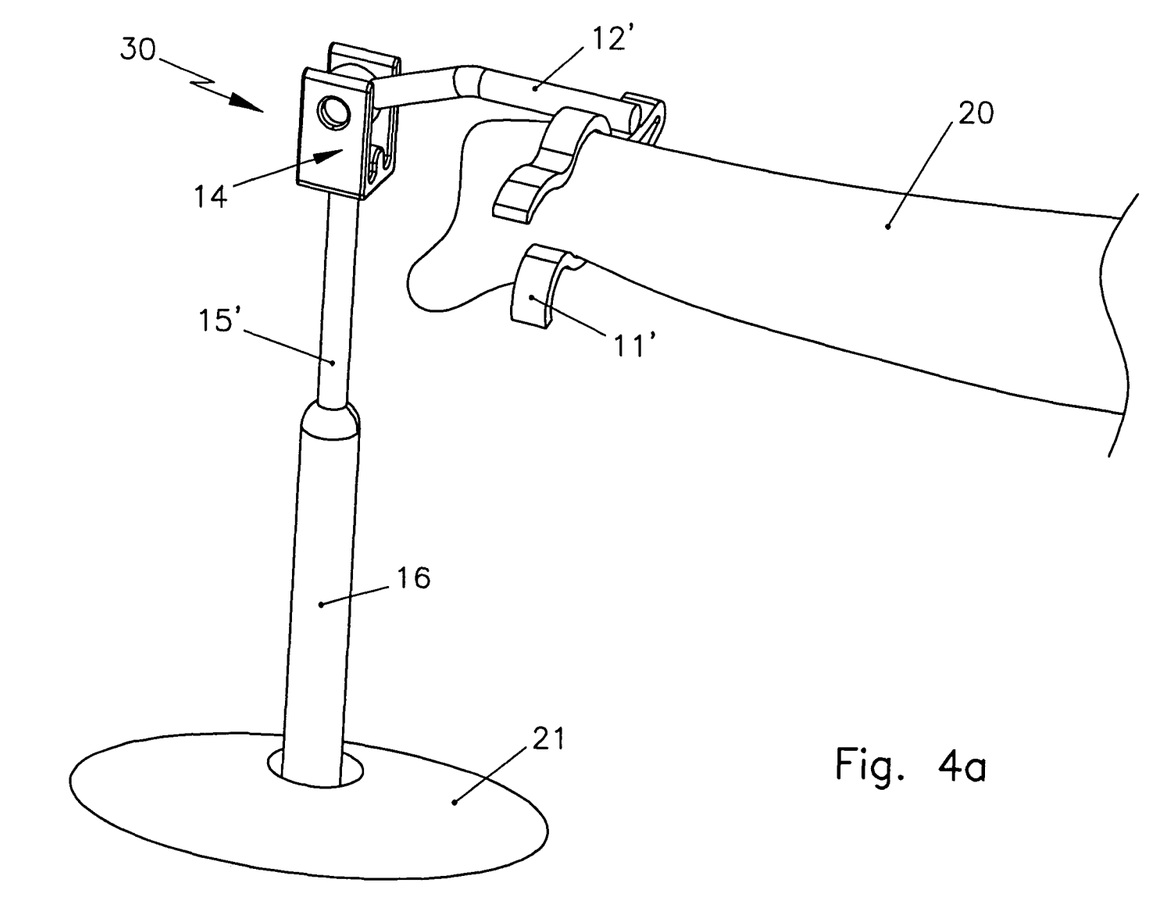
FIG. 4a shows a form of embodiment of the auditory ossicle prosthesis in accordance with the invention with attachment to the anvil projection on the one hand, joint and penetration through the stapes base plate, FIG. 4b as FIG. 4a, but with a longer lever between the anvil projection and joint, FIG. 4c as FIG. 4b, but with an additional mass on the prosthesis.

With the auditory ossicle prosthesis 10 shown in FIGS. 1 to 3 a first class of prostheses in accordance with the invention is shown, by way of which via the lever conditions or the tuning of the middle ear can be considerably improved for sound transmission. Further forms of embodiment are shown in the following figures:

FIG. 4a schematically shows an auditory ossicle prosthesis 30 which on one side is again attached via a first clip 11' to the anvil projection 20. Attached to the first clip 11' is a first rod 12' which is connected in an articulated manner via a U-shaped socket component 14 with the second rod 15' which at other end changes to the piston 16, which in this example of embodiment project through an opening in the stapes base plate 21 into the inner ear (which is not shown).

Figure 4B:
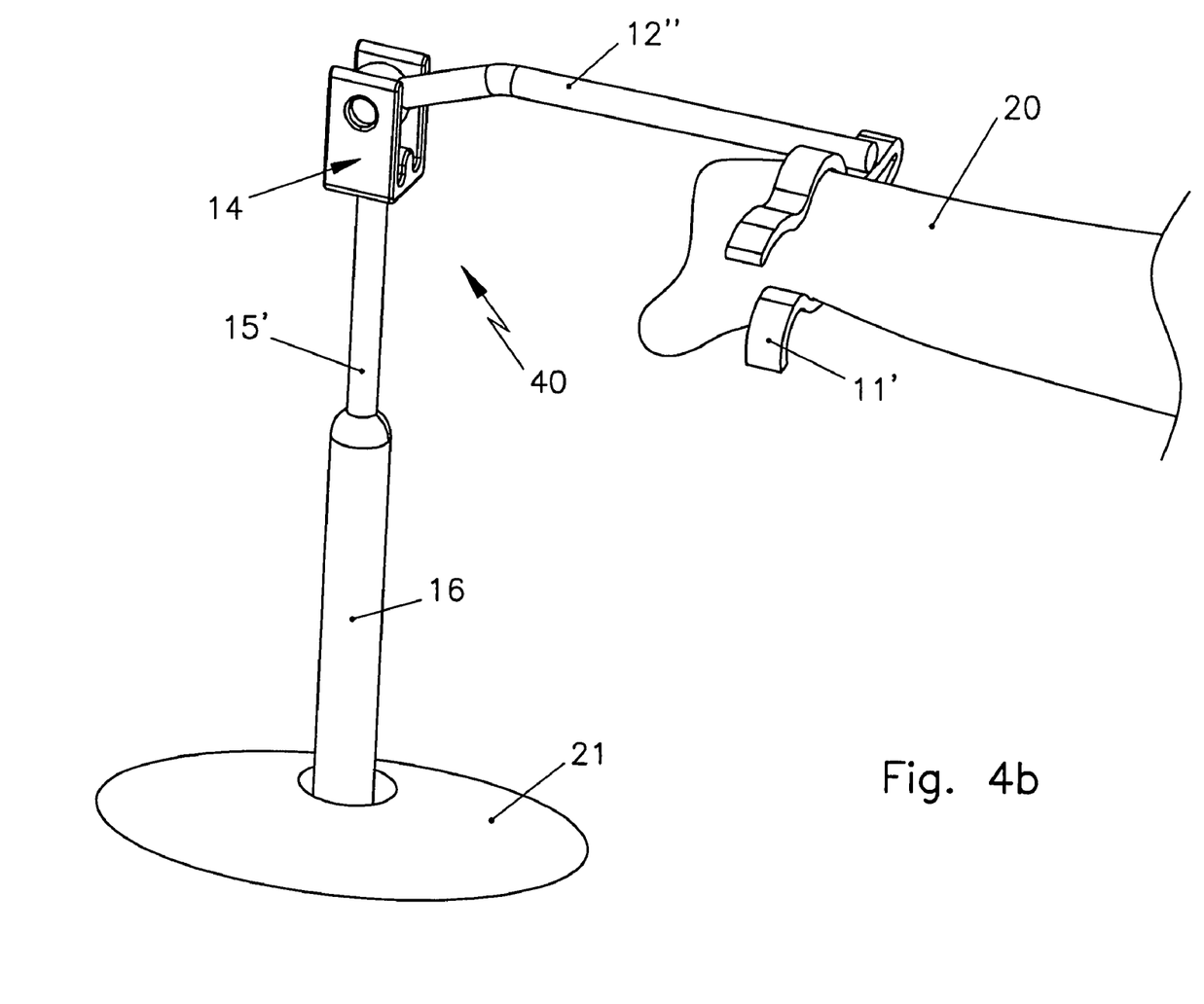

The form of embodiment in accordance with FIG. 4b differs from the one in FIG. 4a in that the first rod 12" of the auditory ossicle prosthesis 40 is considerably prolonged vis-à-vis the first rod 12" of the auditory ossicle prosthesis 30 between the first clip 11' and the articulated end point of the first rod in the ball (not visible in the drawing) of the U-shaped socket component 14, thereby exhibiting a much greater lever path. Depending on the individual situation in the middle ear of the patient, the distance between the first clip 11, 11' and the ball 13 is selected to be in a range of 1 to 5 mm. The distance between the ball 13 and the stapes base plate 21 will be within a range of between 3 and 7 mm.

Figure 4C:
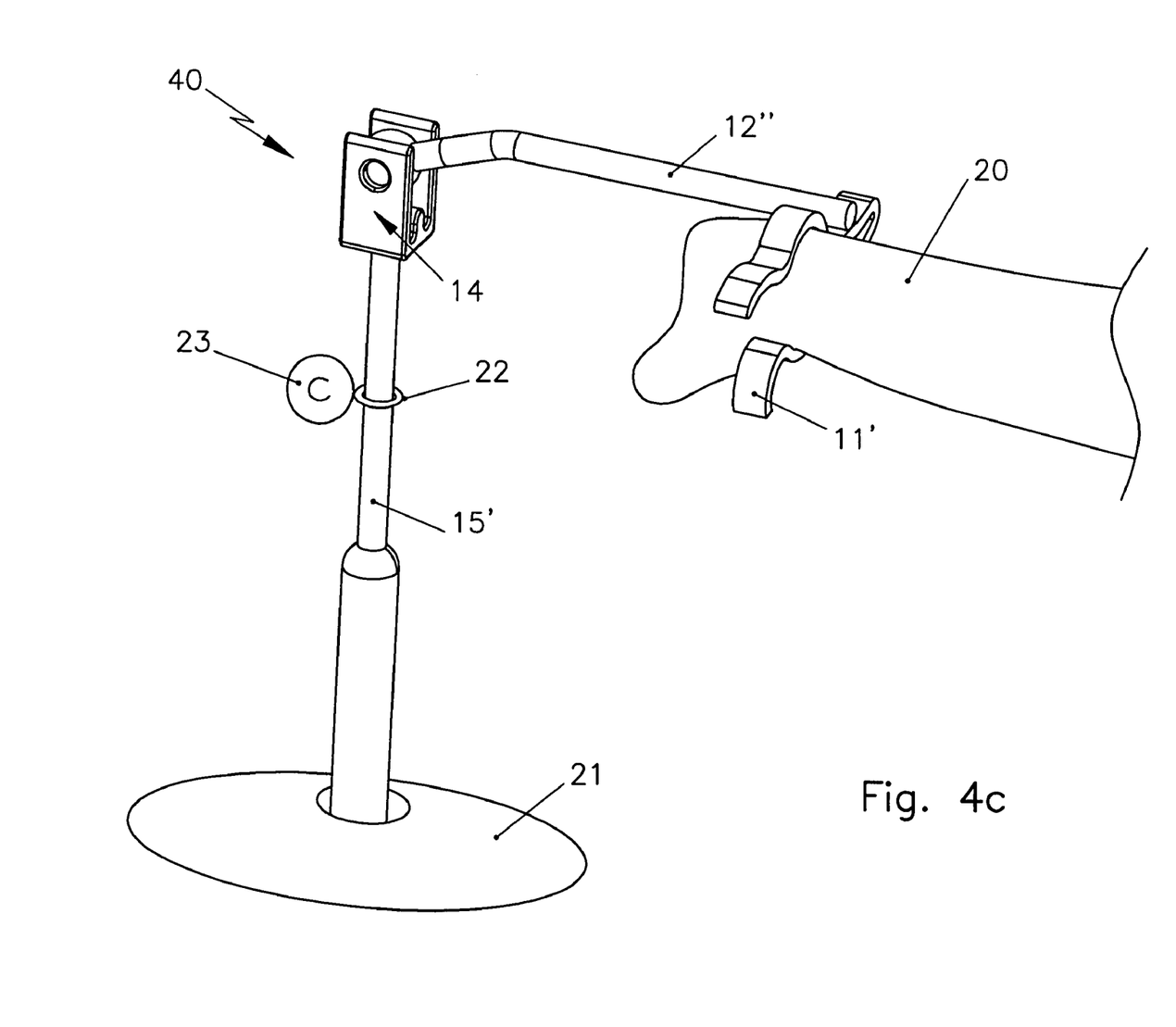

To further improve hearing quality, in the form of embodiment in accordance with FIG. 4c via a clip 22 an additional mass 23 is applied to the rod 15'. This serves to fine tune the acoustic properties of the auditory ossicle prosthesis 40 by specifically shifting the resonance frequency to a desired value.

Figure 5:
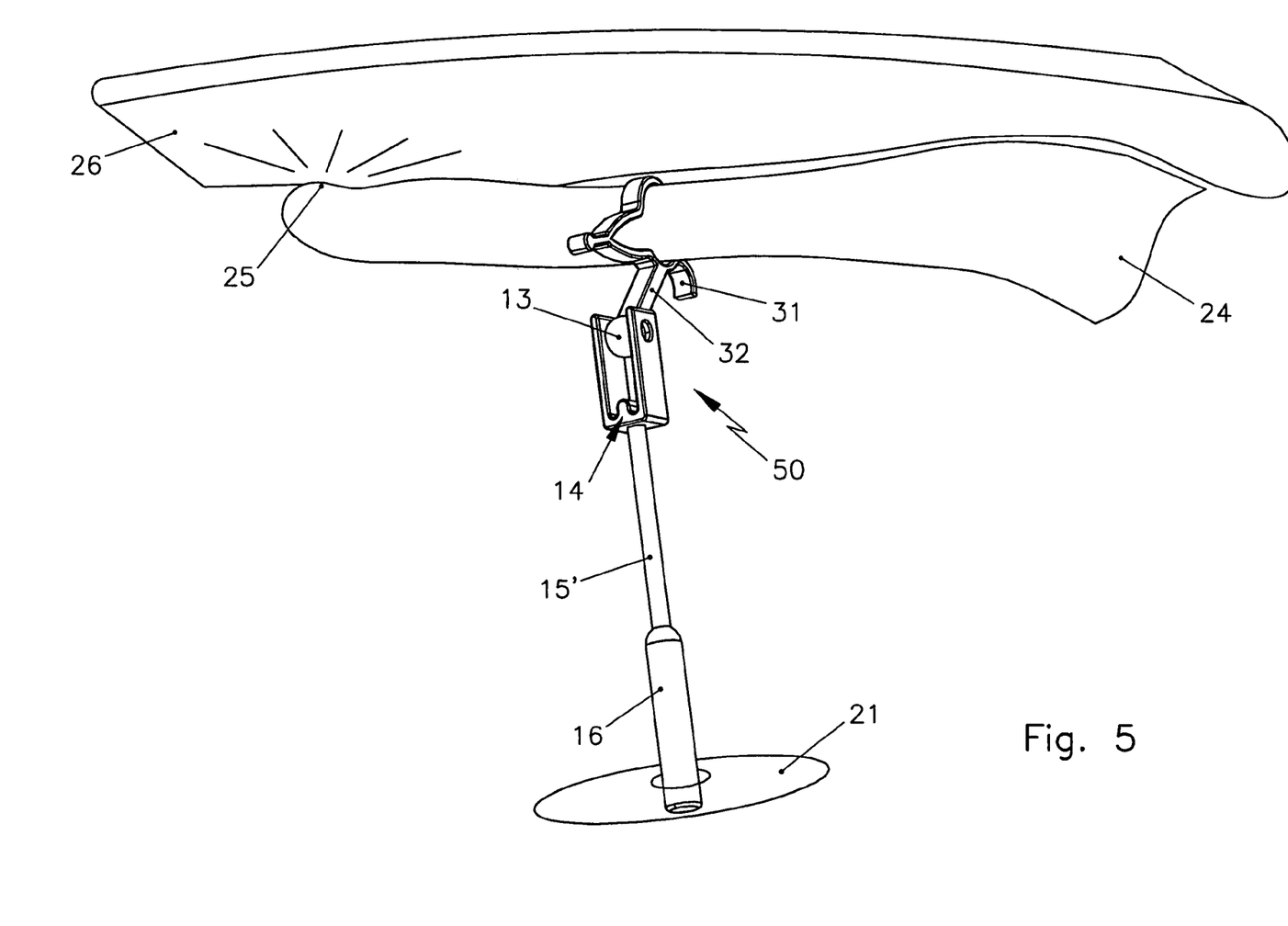
FIG. 5 shows a form of embodiment of the auditory ossicle prosthesis in accordance with the invention with attachment to the hammer grip on the one hand, joint and penetration through the stapes base plate on the other hand.

FIG. 5 shows a further form of embodiment in which the auditory ossicle prosthesis 50 is attached via first clip 31 to the hammer grip 24 in the vicinity of the umbo 25, where the hammer is in mechanical contact with the ear drum 26. Instead of the first rod, in this form of embodiment the clip 31 is connected via an extension 32 directly to the ball 13 of the U-shaped socket component 14, connected to the other end of which is a second rod 15' which changes into the piston 16, which projects via an opening into the stapes plate 21 into the inner ear cavity.

The distance between the ball 13 and the stapes base plate 21 is selected to be in a range between 3 and 6 mm depending on the individual situation of the patient, the distance between the ball 13 and the hammer grip 24 over the length of the extension 23 in a range of 1.5 to 3 mm.

Figure 6:
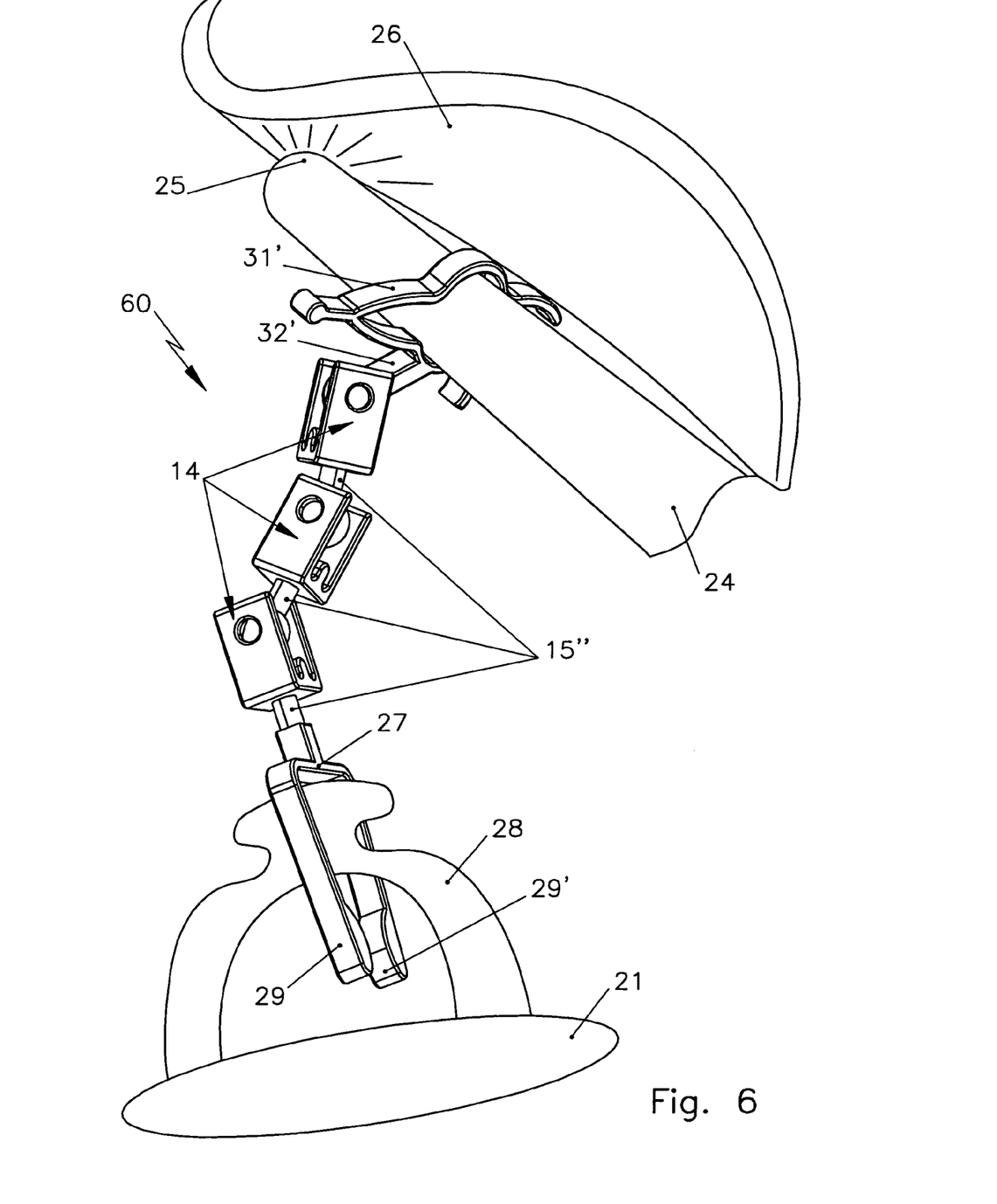
FIG. 6 shows a form of embodiment of the auditory ossicle prosthesis in accordance with the invention with attachment on the hammer grip on the one hand, multiple-element joint and fastening to the stapes bone on the other hand.

Finally, FIG. 6 shows an auditory ossicle prosthesis 60 which as in the form of embodiment in accordance with FIG. 5 is attached at one end via a first clip 31' to the hammer grip 24 in the vicinity of the umbo 25. At its other end the auditory ossicle prosthesis 60 is, however, connected by way of a third clip 27 to the stapes 28. The length of both limbs 29, 29' of the third clip 27 is selected to be in a range of 1 to 3 mm, as a rule between 1.5 and 2.5 mm.

In order to achieve a high degree of articulation, forms of embodiment of the invention can comprise a large number of joint points adjoining each other. The auditory ossicle prosthesis 60 shown in FIG. 6 comprises, for example, three U-shaped socket components 14, connected in the form of a chain by way of shortened rods 15", the first of which is connected to the extension 32' of the first clip 31' and the third via its rod 15'" to third clip 27. The length of the joint chain between the first clip 31' and the third clip 27 is selected in a range of 2 to 6 mm.

The diameter of the ball 13 in the U-shaped socket components 14 is generally around 0.5 mm.

The invention claimed is:

1. An auditory ossicle prosthesis for replacing or bridging at least one element in a human auditory ossicle chain, whereby the auditory ossicle prosthesis is composed of a material selected from the group consisting of an elastic material and a material having at least one articulated connection, the auditory ossicle prosthesis comprising a prosthesis element; means for frequency adjustment of sound transmission in a middle ear, said means for frequency adjustment including lever elements for changing lever conditions in the auditory ossicle chain, wherein said prosthesis element has at least one ball joint connection, wherein said means for frequency adjustment include the lever elements for changing lever conditions in the auditory ossicle chain, whose effective length or lever conditions are changeable in dependence on a predetermined frequency response, wherein said prosthesis element on one side is attachable to an anvil projection and on the other side is attachable to stapes, or is directly inserted into an inner ear, said prosthesis element being configured so that from its connection to the anvil projection it largely copies a course of the natural anvil projection to its end or beyond it and in an area of a natural end of the anvil projection runs at an angle to another end point of the prosthesis element on the stapes or on/in the inner ear, said lever elements including a lever section that extends the natural end of the anvil projection.

2. An auditory ossicle prosthesis as defined in claim 1; and further comprising a first clip for attaching said prosthesis element to the anvil projection, a first rod arranged on said first clip and having an end configured as a ball, a U-shaped socket component in which said ball is arranged and which gradually changes to a second rod that ends as an element selected from the group consisting of a piston and a further clip.

3. An auditory ossicle prosthesis as defined in claim 2, wherein an element selected from the group consisting of said first clip, said further clip, and both has two flexible tongs arranged in a shape selected from the group consisting of a V-shape and a U-shape.

4. An auditory ossicle prosthesis as defined in claim 2, wherein an element selected from the group consisting of said first clip, said further clip, and both is roughened at its point of contact selected from the group consisting of its point of contact with the end projection, its point of contact with the stapes, and both.

5. An auditory ossicle prosthesis as defined in claim 2, wherein an element selected from the group consisting of said first clip, said further clip, and both has a holding grip.

6. An auditory ossicle prosthesis as defined in claim 1, wherein said prosthesis element at one end is directly connected by way of opening human cochlea by cocheotomy.

7. An auditory ossicle prosthesis as defined in claim 6; and further comprising a piston via which said one end of said prosthesis is directly connected.

8. An auditory ossicle prosthesis as defined in claim 1, wherein the prosthesis or parts thereof are composed of a biocompatible synthetic material.

9. An auditory ossicle prosthesis as defined in claim 8, wherein the prosthesis or parts thereof are composed of materials selected from the group consisting of silicon and composite fiber materials.

10. An auditory ossicle prosthesis as defined in claim 1, wherein the prosthesis or parts thereof are composed of a material selected from the group consisting of titanium, gold, tantalum, and an alloy thereof.

11. An auditory ossicle prosthesis as defined in claim 1, wherein the prosthesis or parts thereof are composed of a material with memory effect.

12. An auditory ossicle prosthesis as defined in claim 1, wherein said means for frequency adjustment includes a device for changing a point of attachment of said prosthesis element on an element selected from the group consisting of a hammer, the anvil projection, the stapes, and at the inner ear, in dependence on a predetermined frequency response.

13. An auditory ossicle prosthesis as defined in claim 1; and further comprising at least one additional mass attached to one part of said prosthesis element or the auditory ossicle chain in dependence on a desired, predeterminable frequency response of a sound transmission in the middle ear.

14. An auditory ossicle prosthesis as defined in claim 13; and further comprising a second clip attaching said additional mass to a part of said prosthesis element or the auditory ossicle chain.

15. An auditory ossicle prosthesis as defined in claim 1, wherein said prosthesis element is connected to an active vibration component of a hearing aid; and further comprising means for connecting said prosthesis element to the active vibration component of the hearing aid.

16. An auditory ossicle prosthesis for replacing or bridging at least one element in a human auditory ossicle chain, whereby the auditory ossicle prosthesis is composed of a material selected from the group consisting of an elastic material and a material having at least one articulated connection, the auditory ossicle prosthesis comprising a prosthesis element; means for frequency adjustment of sound transmission in a middle ear, said means for frequency adjustment including lever elements for changing lever conditions in the auditory ossicle chain, wherein said prosthesis element has at least one ball joint connection, and wherein said means for frequency adjustment include the lever elements configured so that effective lengths or lever conditions are changeable depending on a predetermined frequency response.

17. An auditory ossicle prosthesis for replacing or bridging at least one element in a human auditory ossicle chain, whereby the auditory ossicle prosthesis is composed of a material selected from the group consisting of an elastic material and a material having at least one articulated connection, the auditory ossicle prosthesis comprising a prosthesis element; means for frequency adjustment of sound transmission in a middle ear, said means for frequency adjustment including lever elements for changing lever conditions in the auditory ossicle chain, wherein said means for frequency adjustment include the lever elements for changing lever conditions in the auditory ossicle chain, whose effective length or lever conditions are changeable in dependence on a predetermined frequency response, wherein said prosthesis element on one side is attachable to an anvil projection and on the other side is attachable to stapes, or is directly inserted into an inner ear, said prosthesis element being configured so that from its connection to the anvil projection it largely copies a course of the natural anvil projection to its end or beyond it and in an area of a natural end of the anvil projection runs at an angle to another end point of the prosthesis element on the stapes or on/in the inner ear, said lever elements including a lever section that extends the natural end of the anvil projection.

18. An auditory ossicle prosthesis for replacing or bridging at least one element in a human auditory ossicle chain, whereby the auditory ossicle prosthesis is composed of a material selected from the group consisting of an elastic material and a material having at least one articulated connection, the auditory ossicle prosthesis comprising a prosthesis element; means for frequency adjustment of sound transmission in a middle ear, said means for frequency adjustment including lever elements for changing lever conditions in the auditory ossicle chain, and wherein said means for frequency adjustment include the lever elements configured so that effective lengths or lever conditions are changeable depending on a predetermined frequency response.

* * * * *